United States Patent [19]

Michalos

[11] Patent Number: 4,923,693

[45] Date of Patent: May 8, 1990

[54] ULTRAVIOLET RADIATION SCREENING METHOD FOR EYES

[75] Inventor: Peter Michalos, Brooklyn, N.Y.

[73] Assignee: Sundrops Enterprises, Inc., Boca Raton, Fla.

[21] Appl. No.: 146,346

[22] Filed: Jan. 21, 1988

[51] Int. Cl.$^5$ .......................... A61K 7/40; A61K 7/42; A61K 33/00

[52] U.S. Cl. ...................................... 424/59; 514/912; 514/915; 514/944; 514/954; 514/969

[58] Field of Search ........................ 514/954, 915, 912; 424/59

[56] References Cited

U.S. PATENT DOCUMENTS 4,436,730  3/1984  Ellis et al. ............................ 514/915
4,744,980  5/1988  Holly ..................................... 514/915
4,748,189  5/1988  Su et al. ............................... 514/912

FOREIGN PATENT DOCUMENTS 2169508  7/1986  United Kingdom ................ 514/915

OTHER PUBLICATIONS

Ensley, The Optician, 6/1959, vol. 137, pp. 543 to 548.

*Primary Examiner*—Dale R. Ore

[57] ABSTRACT

An inventive method for preventing ultraviolet radiation exposure to the outer tissues of mammalian eyes is disclosed. In particular, the composition containing about 0.3%–0.4% hydroxypropylmethylcellulose in the form of either an eyedrop solution or an ointment is applied to the eyes prior to exposure to UV radiation.

5 Claims, No Drawings

ULTRAVIOLET RADIATION SCREENING METHOD FOR EYES

FIELD OF THE INVENTION

The invention relates to a method using an opthalmic agent for protecting mammalian eyes from the harmful effects of ultraviolet radiation. In particular, a composition containing hydroxypropylmethylcellulose is placed in mammalian eyes to block UV radiation to provide a sunscreen and to help minimize such exposure.

BACKGROUND OF THE INVENTION

Ultraviolet radiation exposure of mammalian eyes has been associated with the growth of the eye disease pterygia and the promotion of the conversion of pinguecula to pterygia (American Academy of Opthalmology, Basic and Clinical Science Course, Cornea Section 4, Retina Vitress 1987-1988 Edition, pp. 72-73).

Pinguecula is a benign eye disease in which a yellow, triangular patch forms on the conjunctiva and covers the sclera. When such a patch encroaches onto the cornea and forms a thickened, vascular and wing-shaped area of the conjunctiva the resulting condition is known as pterygia which may block the visual axis. It is known that ultraviolet light irritates the outer membranes of the eye and further stimulates the conversion of one disease into another. A theoretical possibility of the role of UV light in the formation of tumors in the retina, such as melanoma, may exist. Also non entity called "solar retinopathy" has been described in which the retina may be damaged by UV light (Ham, W. T., et al., *Solar Retinopathy as a Function of Wavelength: Its Significance for Protective Eyewear*, pp. 319-346; Ham W. T., *Ocular Hazards of Light Sources*, Review of Current Knowledge. J. Occup. Med. 25: 101-103, 1983.

The only means known in the art to shield the outer eye membranes from harmful ultraviolet radiation having a wavelength in the range of 290-320 nanometers, is the physical blocking of the radiation by means of sunglasses or other sunscreen devices physically attached to the face or head of the user. There are no opthalmic sunscreen agents known in the prior art until now.

Various compositions and mixtures thereof were considered for use as the opthalmic agent in the inventive method and discarded as ineffective. For example, p-aminobenzoic acid (PABA) blocks UV radiation but is too irritating to the delicate tissues of the eye and interferes with other antibiotic solutions which may be used by the patient following surgical removal of the pterygia bodies. Additionally, preparation of a solution containing PABA for use in the eye is quite costly.

Existing opthalmic solutions which may be obtained commercially without a prescription and which are used to lubricate eye tissues forming artificial tears to relieve irritation of the eyes are known. In general, these known solutions may be divided into two types: eyedrop solutions containing polyvinylchlorides and those containing hydroxypropylmethylcellulose.

Polyvinylchloride containing solutions were found to be wholly ineffective in blocking UV radiation from the eyes as illustrated in Table 1 infra.

It has been unexpectedly shown that hydroxypropylmethylcellulose containing compositions do effectively block UV radiation and thus may help prevent the occurrence of solar related ocular pathology as discussed above.

SUMMARY OF THE INVENTION

The objects discussed above and those objects which will be obvious to those skilled in the art are accomplished by applying a composition containing hydroxypropylmethylcellulose to the outer membranes of the eye in the form of either an eyedrop solution, ointment, gel or any other suitable means known in the art, preferably prior to exposure of the eyes to ultraviolet radiation.

In particular, the composition contains about 0.5 percentage hydroxypropylmethylcellulose by volume of a solution. The composition may also be prepared with Dextran 40, sodium chloride, potassium chloride and perservatives such as benzalkoniumchloride and EDTA.

DETAILED DESCRIPTION OF THE PREFERRED EMBODIMENTS

The method utilizes a composition and its principal ingredient is hydroxypropylmethylcellulose, preferably 0.3%-0.4% by volume of the composition solution.

Other ingredients of the composition may include Dextran 40, preferably 0.1% by volume of the solution, sodium chloride, potassium chloride and perservatives. Preferable perservatives include benzalkoniumchloride, preferably 0.01% by volume of the solution, and EDTA. Purified water buffered with sodium borate and boric acid may also be included.

An example of such a composition is manufactured and sold under the trademark, MOISTURE DROPS owned by Bausch & Lomb.

In the preferable form, the composition is contained in a solution which may be applied as drops to the outer tissues of the eye to absorb and transmit wavelengths of ultraviolet radiation.

Another preferable form of the composition is an ointment or ocular emollient. Such an ointment contains approximately 50% sterile white petroleum mineral oil. Other colloidal delivery systems which are possible include the use of pH sensitive nonparticles (latex systems) described by Gurny and co-workers (1985) or eye temperature sensitive Sol-gel transition systems. Color tint may also be incorporated in the eyedrops. It may be appreciated that any carrier form which would be suitable for applying the composition to the outer tissues of the eye would be acceptable.

UV SPECTROPHOTOMETER TEST RESULTS

Spectrophotometer tests were performed with a Bausch & Lomb UV spectrophotometer manufactured by Bausch & Lomb, by diluting solutions of 0.5% hydroxypropylmethylcellulose with sterile water in a ratio of 1:3 hydroxpropylmethylcellulose to water. Dilution was carried out to simulate the mixing effect of the hydroxpropylmethylcellulose with human tears. Taking into account that normal tear film volume in man is approximately 7 ml (microliters) and a tear turnover of 1.2 ml per minute (Lee and Robinson, 1986). Distilled water was used as a control in the experiment. Wavelengths of light radiation ranging from 270-320 nanometers were used to test the absorbance and transmission of the hydroxypropylmethylcellulose containing solution. The experiment was repeated four times and results averaged to obtain the following test results presented in Table 1.

TABLE 1

Experimental Data

| wavelength | absorbance | % transmission |
|---|---|---|
| 270 | .28 | 52% |
| 280 | .46 | 35% |
| 290 | .39 | 41% |
| 295 | .25 | 56% |
| 300 | .15 | 71% |
| 310 | .06 | 87% |
| 320 | .035 | 92% |

Comparison Data

| wavelength | absorbance of distilled water | absorbance of polyvinyl chloride and water |
|---|---|---|
| 270 | 0 | 0 |
| 280 | 0 | 0 |
| 290 | 0 | 0 |
| 295 | 0 | 0 |
| 300 | 0 | 0 |
| 310 | 0 | 0 |
| 320 | 0 | 0 |

The above procedure was also used to test the effectiveness of aqueous polyvinylchloride solutions and as illustrated in Table 1 supra this solution had no more effectiveness in blocking UV radiation than distilled water alone.

As illustrated above, in the range of wavelengths corresponding to ultraviolet radiation (i.e. 290-320) the solution containing hydroxypropylmethylcellulose transmitted from 41 to 92% of the test UV wavelengths, such that about 0.035 of the UV light was absorbed by the eyedrops when the wavelength equalled 320 nanometers. Further, an absorption value of 0.39 was observed when the wavelength was 290 nanometers.

When the hydroxpropylmethylcellulose containing composition in the form of an ointment was tested in the Bausch & Lomb spectrophotometer according to the foregoing experimental parameters, it was found that at least 15% more UV light was absorbed when compared to the absorbance values of the hydroxypropylmethylcellulose containing solution. The ointment form is preferable because of increased ocular residence time thus prolonging action time to screen harmful UV radiation during outdoor activities in the sun, such as beach going, outdoor sports, etc which involve greater durations. It may be noted, however, that the eye drop form of the composition may be considered more convenient by some people.

Tests using Gamma Scintigraph (a noninvasive test) are planned to track retention and precorneal clearance of this ophthalmic formulation by use of a special computerized gamma camera which outlines the path of opthalmic drugs once they are instilled in the eye.

I claim:

1. A method for minimizing the effect of ultraviolet radiation on mammalian eyes comprising applying an effective amount of a composition containing hydroxypropylmethylcellulose in a carrier to the outer tissues of the mammalian eyes.

2. The method according to claim 1 further comprising applying the composition to the mammalian eyes prior to exposure of the eyes to ultraviolet radiation.

3. The method according to claim 1 wherein the composition comprises hydroxypropylmethylcellulose in the range of about 0.3%–0.4% by volume of the composition.

4. The method according to claim 3 wherein the composition further comprises, sodium chloride, potassium chloride, benzalkoniumchloride and EDTA.

5. The method according to claim 3 wherein the hydroxypropylmethylcellulose is incorporated into a carrier in the form of an eyedrop solution, an ointment, or a gel.

* * * * *